United States Patent [19]

Wong et al.

[11] Patent Number: 5,342,767
[45] Date of Patent: Aug. 30, 1994

[54] LACTOBACILLUS KEFIR ALCOHOL DEHYDROGENASE

[75] Inventors: Chi-Huey Wong, Rancho Santa Fe; Curt W. Bradshaw, San Diego, both of Calif.

[73] Assignee: The Scripps Research Institute, La Jolla, Calif.

[21] Appl. No.: 85,347

[22] Filed: Jun. 30, 1993

Related U.S. Application Data

[62] Division of Ser. No. 841,701, Feb. 26, 1992, Pat. No. 5,225,339.

[51] Int. Cl.$^5$ .................. C12P 9/00; C12P 11/00; C12P 17/12; C12P 7/26
[52] U.S. Cl. ........................ 435/122; 435/126; 435/130; 435/131; 435/148; 435/189; 435/190; 435/280; 435/853
[58] Field of Search .............. 435/122, 126, 130, 131, 435/189, 190, 280, 853, 148

[56] References Cited

U.S. PATENT DOCUMENTS 5,225,339  7/1993  Wong et al. .................. 435/122

OTHER PUBLICATIONS

Hummel et al., *Eur. J. Biochem.*, 184:1 (1989).
Whitesides et al., *Angew. Chem. Int. Ed. Engl.*, 24:617 (1985).
Keinan et al., *J. Am. Chem. Soc.*, 108:162 (1986).
Keinan et al., *J. Am. Chem. Soc.*, 108:3474 (1986).
Drueckhammer et al., *Enzyme Microb. Technol.*, 9:564 (1987).
Drueckhammer et al., *J. Org. Chem.*, 53:1607 (1988).
Prelog, V., *Pure Appl. Chem.*, 9:119 (1964).
Hummel, W., *Appl. Microb. Biotechnol.*, 34:15 (1990).
Guillerm et al., *Tetrahedron Letts.*, 48:5857 (1986).
El Ali et al., *J. Org. Chem.*, 56:5357 (1991).
Herold et al., *J. Org. Chem.*, 54:1178 (1989).
Sokolov et al., *Gazzette Chim. Ital.*, 117:525 (1987).
Syidatk et al., *Biotechnol. Lett.* 10:731 (1988).
Burgess et al., *J. Am. Chem. Soc.*, 113:6129 (1991).
Arnold et al., *Biochemistry*, 15:4844 (1976).
Dale et al., *J. Org. Chem.*, 34:2543 (1969).
Peters et al., *J. Org. Chem.*, 33:4245 (1968).
Ziffer et al., *J. Org. Chem.*, 48:3017 (1983).
Lundkvist et al., *J. Med. Chem.*, 32:863 (1989).
Walton et al., *J. Organometal. Chem.*, 37:45 (1972).
Birkofer et al., *Chem. Ber.*, 112:2829 (1979).
Yogo et al., *Synth. Commun.*, 11:769 (1981).
Brinkmeyer et al., *J. Am. Chem. Soc.*, 99:8339 (1977).
Earl et al., *J. Org. Chem.*, 49:4786 (1984).
Merault et al., *J. Organomet. Chem.*, 76:17 (1974).
Birkofer et al., *Chem. Ber.*, 120:1059 (1987).

*Primary Examiner*—Herbert J. Lilling
*Attorney, Agent, or Firm*—Welsh & Katz, Ltd.

[57] ABSTRACT

The present invention discloses the preparation of R-configured trialkylsilylethynyl α-alcohols from similarly substituted α-ketones, and vice versa, catalyzed by the alcohol dehydrogenase of *Lactobacillus kefir*, ATCC No. 35411. Also disclosed is the acceptance or transfer of a hydride ion from or to the pro-R face of NADPH or NADP, respectively, as catalyzed by that enzyme.

6 Claims, No Drawings

LACTOBACILLUS KEFIR ALCOHOL DEHYDROGENASE

This invention was made with the support of the United States Government under National Institutes of Health Contract GM 44154 and the U.S. Government has certain rights in the invention.

This is a division of co-pending application Ser. No. 07/841,701, filed Feb. 26, 1992, now U.S. Pat. No. 5,225,339, issued Jul. 6, 1993.

TECHNICAL FIELD OF THE INVENTION

The present invention relates to processes for forming R-configured trialkylsilylethynyl α-alcohols and ketones from such alcohols using the *Lactobacillus kefir* alcohol dehydrogenase enzyme, and for transferring a hydride ion from an R-configured alcohol to the pro-R face of NADP or transferring a hydride ion from the pro-R face of NADPH to the si face of a carbonyl group of a ketone using that enzyme.

BACKGROUND OF THE INVENTION

Alcohol dehydrogenases are well established enzymes that catalyze the interconversion of carbonyl compounds and alcohols. See. e.g., Hummel et al., *Eur. J. Biochem.*, 184:1 (1984); Whitesides et al., *Angew. Chem. Int. Ed, Engl.*, 24:617 (1985); Lemiere, "Enzymes as Catalysts in Organic Synthesis" (Schneider, M.P. ed.), D. Reidel Publishing: 1986, pp 19–34; Jones, J.B. et al., in "Applications of Biochemical Systems in Organic Synthesis" (Jones, J.B., et al. eds.), John Wiley and Sons: New York, 1976, pp 248–376; Jones, J.B., "Mechanisms of Enzymatic reactions: Stereochemistry" (Frey, P.A. ed.) Elsevier Science: 1986, 3–14; Jones, J.B., "Enzymes in Organic Synthesis," Ciba Foundation Symposium III, Pitman: London, 1985, pp. 3–14; Keinan et al., *J. Am. Chem. Soc.*, 108:162 (1986); Keinan et al., *J. Am. Chem. Soc.*, 108:3474 (1986); Drueckhammer et al., *Enzyme Microb. Technol.*, 9:564 (1987); Drueckhammer et al., *J. Org. Chem.*, 53:1607 (1988).

The most extensively used and studied alcohol dehydrogenases have been obtained from horse liver, yeast and the bacterium *Thermoanaerobium brockii*.

Alcohol dehydrogenase action involves the transfer of a hydride between a substrate (an alcohol or an aldehyde or ketone; i.e., a carbonyl, substrate) and a cofactor, which serves as a hydride acceptor or donor. Typically, the cofactor for alcohol dehydrogenase is nicotinamide adenine dinucleotide (NAD), reduced nicotinamide adenine dinucleotide (NADH), nicotinamide adenine dinucleotide phosphate (NADP), or reduced nicotinamide adenine dinucleotide phosphate (NADPH).

NAD and NADP are major electron (e⁻) acceptors in the oxidation of molecules. The reactive part of NAD or NADP is the nicotinamide ring.

In the oxidation of a substrate molecule such as an alcohol, that nicotinamide ring accepts a hydride ion and is reduced. As used herein, the phrase "hydride ion" means H⁻ (a proton associated with two electrons), deuteride (D⁻) (a deuterium ion associated with two electrons) or tritide (T⁻) (a tritium ion associated with two electrons). These three isotopic hydride ions can also be referred to as $^1$H⁻, $^2$H⁻ and $^3$H⁻.

Any of those hydride ions can be used to reduce NAD or NADP. The reduced forms of NAD and NADP are referred to herein as NADH and NADPH, respectively. By way of example, the structure of NADH is shown below.

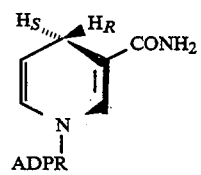

The two depicted hydrogens bonded to the nicotinamide ring of NADH are designated $H_S$ and $H_R$. Those designations are used to indicate the spatial orientation of those hydrogens. The $H_S$ hydrogen has the S configuration and the $H_R$ hydrogen has the R configuration.

Where NADH or NADPH serves as a hydride donor for alcohol dehydrogenase activity, the hydride can be either the $H_S$ or the $H_R$. Conversely, where NAD or NADP serves as the hydride acceptor for alcohol dehydrogenase activity, the added hydride can be either the $H_S$ or the $H_R$.

Where the added or donated hydride is $H_R$, the alcohol dehydrogenase is said to act on the pro-R face of the cofactor. Where the added or donated hydride is $H_S$, the alcohol dehydrogenase is said to act on the pro-S face of the cofactor.

The carbonyl substrates for alcohol dehydrogenase action exist in two potentially diastereotopic forms, where the side chains attached to the carbonyl carbon are different. Two such arrangements are shown in formulae III and IV, below, where the side chain groups X and Y are of different size (i.e. molecular weight) with X>Y.

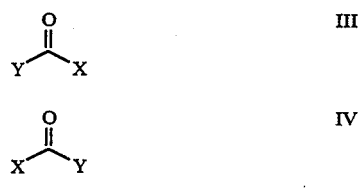

If the two groups by standard sequence rules have the order X>Y, that face in which the O>X>and Y groups are placed in a plane and arranged in a clockwise manner (formula III, above) is referred to as the re face, That face in which the three groups are similarly placed in a plane and arranged in a counterclockwise manner (formula IV, above) is referred to as the si face.

Alcohol dehydrogenases that follow Prelog's Rule produce alcohols wherein the carbon atom bearing the formed hydroxyl group has the S configuration. Alcohol dehydrogenases that follow Anti-Prelog's Rule produce alcohols wherein the carbon atom bearing the formed hydroxyl group has the R configuration.

In view of the known cofactor and substrate stereoconfigurations, it can be seen that alcohol dehydrogenases can work in one of four ways. Those four possible mechanisms are illustrated below in Scheme 1 and are designated $E_1$, $E_2$, $E_3$ and $E_4$.

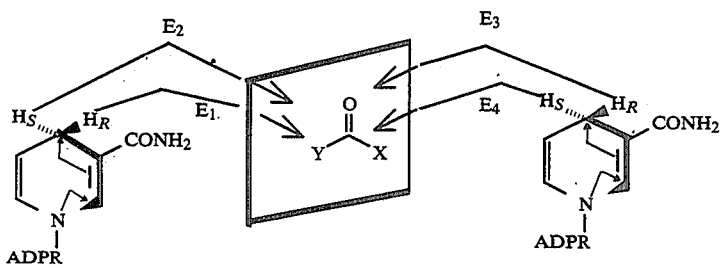

The $E_1$ mechanism is characterized by specificity for the pro-R hydrogen of the cofactor and addition of a hydride ion to the Si face of a carbonyl substrate. The $E_2$ mechanism is characterized by specificity for the pro-S hydrogen of the cofactor and addition of a hydride ion to the Si face of a carbonyl substrate. The $E_3$ mechanism is characterized by specificity for the pro-R hydrogen of the cofactor and addition of a hydride ion to the Re face of a carbonyl substrate. The $E_4$ mechanism is characterized by specificity for the pro-S hydrogen of the cofactor and addition of a hydride ion to the Re face of a carbonyl substrate.

The previously described alcohol dehydrogenases from horse liver, yeast and *Thermoanaerobium brokii* are all characterized as operating via the $E_3$ mechanism (i.e., they catalyze the transfer of a hydride ion from the pro-R face of the cofactor to the Re face of a carbonyl substrate to produce an alcohol having the S configuration. Prelog, *Pure Appl. Chem.*, 9:119 (1964).

An alcohol dehydrogenase has been isolated from *Mucor javanicus* and found to operate via the $E_2$ mechanism.

Recently, an alcohol dehydrogenase enzyme has been isolated from Pseudomonas sp. strain SBD6. That enzyme was found to operate via the $E_1$ mechanism.

Alcohol dehydrogenases can be further characterized by their specificity for certain cofactors and their ability to act on substrates of varying structural complexity. In this regard, alcohol dehydrogenases can, typically, use either but not both of NAD(H) or NADP(H).

The alcohol dehydrogenases from Pseudomonas sp. strain SBD6, horse liver, yeast and *Thermoanaerobium brokii* require that the carbonyl or hydroxyl group of the substrate be adjacent to a methyl group. The *Lactobacillus kefir* alcohol dehydrogenase can use such methyl-substituted substrates, but this enzyme is not limited to such substrates. Rather, this enzyme can use substrates having aromatic, aliphatic and cyclic side chains. Hummel, *Appl. Microb. Biotechnol.* 34:15 (1990).

In view of the foregoing, it can be seen that there is no predictable relationship between carbonyl substrate structural specificity and hydride transfer mechanism for known alcohol dehydrogenases.

BRIEF SUMMARY OF THE INVENTION

The present invention relates to an alcohol dehydrogenase enzyme from *Lactobacillus kefir*. The present invention demonstrates that the *Lactobacillus kefir* alcohol dehydrogenase uses the $E_1$ mechanism of hydride transfer. The present invention also demonstrates that the *Lactobacillus kefir* alcohol dehydrogenase accepts silicon-containing carbonyl substrates to form R-configured silicon-containing alcohols. This is the first report of an alcohol dehydrogenase enzyme that can form these important compounds.

The present invention contemplates the preparation of silicon-containing alcohols and ketones using the alcohol dehydrogenase enzyme from *Lactobacillus kefir*. The present invention further contemplates the use of that enzyme to transfer a hydride ion from an R-alcohol to the pro-R position of NADP to form NADPH and a ketone. The present invention still further contemplates the use of that enzyme to transfer a hydride ion from the pro-R position of NADPH to the si face of a carbonyl group of a ketone to form NADP and an R-alcohol.

More specifically, the present invention contemplates a process for the preparation of an R-configured trialkylsilylethynyl s-containing alcohol by forming a reaction mixture in a liquid medium by admixing (i) NADPH, (ii) a catalytic amount of the alcohol dehydrogenase enzyme from *Lactobacillus kefir*, ATCC designation 35411, and (iii) a trialkylsilylethynyl α-ketone substrate of formula I, below:

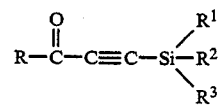

wherein R is selected from the group consisting of $C_1$–$C_6$ alkyl, $C_1$–$C_6$ alkenyl, $C_1$–$C_6$ haloalkyl and $C_1$–$C_3$ alkyl $C_1$–$C_3$ alkylenecarboxylate, and whose chain length is that of one to about six carbon atoms; and $R^1$, $R^2$, and $R^3$ are the same or different, and each is selected from the group consisting of $C_1$–$C_4$ alkyl.

The reaction mixture is then maintained under biological reaction conditions and for a time period sufficient to reduce the silicon-containing ketone and form a silicon-containing alcohol of the corresponding formula.

The invention also contemplates a process for the preparation of a trialkylsilylethynyl α-ketone product by forming a reaction mixture in a liquid medium by admixing (i) NADP, (ii) a catalytic amount of the alcohol dehydrogenase enzyme from *Lactobacillus kefir*, ATCC designation 35411, and (iii) an R-configured trialkylsilylethynyl α-alcohol of formula Ia, below:

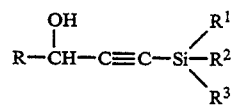

wherein R, its chain length and $R^1$, $R^2$ and $R^3$ are as defined before.

The reaction mixture is then maintained under biological reaction conditions and for a time period sufficient to oxidize the trialkylsilylethynyl α-alcohol and form a trialkylsilylethynyl α-ketone of the corresponding formula.

The invention further contemplates a process for transferring a hydride ion from an R-alcohol substrate to the pro-R position of NADP by forming a reaction mixture in a liquid medium by admixing (i) NADP, (ii) a catalytic amount of the alcohol dehydrogenase enzyme from *Lactobacillus kefir*, ATCC designation 35411, and (iii) an R-alcohol of formula II, below:

wherein $R^5$ is selected from the group consisting of phenyl, furanyl, thiophenyl, pyridyl, indoyl, biphenylyl, $C_1$–$C_3$ alkylenephenyl, $C_2$–$C_3$ alkenylenephenyl, $C_2$–$C_3$ oxaalkylenephenyl, $C_1$–$C_6$ alkenyl, $C_1$–$C_3$ alkyl, $C_1$–$C_6$ haloalkyl, $C_1$–$C_6$ oxoalkyl, $C_1$–$C_6$ halooxoalkyl, and $C_1$–$C_3$ alkylenecarboxylate;

$R^4$ is hydrogen, $C_1$–$C_6$ alkyl, $C_1$–$C_6$ haloalkyl, $C_1$–$C_4$ trialkylsilylethynyl, $C_1$–$C_6$ azaalkyl, $C_1$–$C_6$ oxaalkyl, $C_1$–$C_6$ alkoxy carbonyl, $C_1$–$C_6$ acyl and $C_1$–$C_6$ oxoalkyl;

or $R^4$ and $R^5$ together form a 5-, 6- or 7-membered saturated or monoethylenically unsaturated ring;

$R^6$ is hydrogen, deuterium or tritium; and the total chain length of a substrate of formula II is three to about 10 carbon atoms.

The reaction mixture is then maintained under biological conditions and for a time period sufficient to transfer the hydride ion from the R-configured alcohol to NADP and form NADPH and a ketone of the corresponding formula.

The present invention still further contemplates a process for transferring a hydride ion from the pro-R position of NADPH to the si face of a carbonyl group of a ketone by forming a reaction mixture by admixing in a liquid medium (i) NADPH, (ii) a catalytic amount of the alcohol dehydrogenase enzyme from *Lactobacillus kefir*, ATCC designation 35411, and (iii) a ketone substrate of the formula IIa, below:

wherein $R^4$, $R^5$ and the total chain length of the substrate are as defined before.

The reaction mixture is then maintained under biological conditions and for a time period sufficient to transfer a hydride ion from the pro-R position of NADPH to the si face of the carbonyl group of the ketone and form NADP and an R-configured alcohol of the corresponding formula.

The present invention has several benefits and advantages.

A major benefit is that the *Lactobacillus kefir* alcohol dehydrogenase enzyme can accept silicon-containing substrates, thereby providing a novel method of making important trialkylsilylated α-hydroxyl alkyne derivatives. For example, compounds such as (R)-1-trimethylsilyl-1-butyn-3-ol (Compound 8a) and methyl-4-hydroxy-1-trimethylsilyl-5-hexynoate (Compound 9a) are useful as intermediates in the synthesis of leukotrienes [Guillerm et al., *Tetrahedron Letts.*, 48:5857 (1986)], 2(5H)-furanones [El Ali et al., *J. Org. Chem.*, 56:5357 (1991)], and peptide isosteres [Herold et al., *J. Org. Chem.*, 4:1178 (1989)].

An advantage of synthesizing such compounds using the *Lactobacillus kefir* alcohol dehydrogenase enzyme is that the compounds are typically produced in enantiomeric excess of greater than about 90 percent, and usually greater than about 95 percent.

Another benefit is the ability of the enzyme to add a hydride ion to the pro-R face of NADP, providing a method for preparing NADPH with a label at a known position. For example, a deuterium label can be transferred to the pro-R position of NADP by the alcohol dehydrogenase of *Lactobacillus kefir*, producing a deuterated NADPH. This deuterated NADPH is useful as a probe to examine the mechanism of action of enzymes that use NADPH as a co-factor.

Still further benefits and advantages of the invention will be apparent to the skilled worker from the disclosure that follows.

DETAILED DESCRIPTION OF THE INVENTION

A. Processes

The present invention contemplates four related processes. Each of these processes utilizes an alcohol dehydrogenase enzyme from *Lactobacillus kefir*. Two of those processes relate to the reduction or oxidation of a trialkylsilylethynyl ketone or R-configured alcohol, respectively, to the corresponding R-configured alcohol or ketone, respectively. The other two processes relate to the oxidation or reduction of NADPH or NADP, respectively, to NADP or NADPH with a concomitant hydride transfer or acceptance at the pro-R face of the cofactor. Those four processes are broadly set out below, followed by a detailed discussion.

1. Process of forming an R-configured trialkylsilylethynyl α-alcohol

In one aspect, the present invention contemplates a process for the preparation of an R-configured trialkylsilylethynyl α-alcohol comprising the steps of:

(a) forming a reaction mixture in a liquid medium by admixing (i) NADPH, (ii) a catalytic amount of the alcohol dehydrogenase enzyme from *Lactobacillus kefir*, ATCC designation 35411, and (iii) a trialkylsilylethynyl α-ketone substrate of formula I, below:

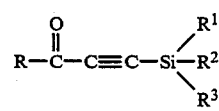

wherein R is selected from the group consisting of $C_1$–$C_6$ alkyl, $C_1$–$C_6$ alkenyl, $C_1$–$C_6$ haloalkyl and $C_1$–$C_3$ alkyl $C_1$–$C_3$ alkylenecarboxylate, and whose chain length is that of one to about six carbon atoms; and $R^1$, $R^2$ and $R^3$ are the same or different, and each is selected from the group consisting of $C_1$–$C_4$ alkyl; and (b) maintaining the reaction mixture under biological reaction conditions and for a time period sufficient to reduce the trialkylsilylethynyl α-ketone and form an R-configured trialkylsilylethynyl α-alcohol of the corresponding formula.

2. Process of forming a trialkylsilylethynyl α-ketone

In another aspect, the present invention contemplates a process for the preparation of a trialkylsilylethynyl α-ketone comprising the steps of (a) forming a reaction mixture in a liquid medium by admixing (i) NADP, (ii) a catalytic amount of the alcohol dehydrogenase enzyme from *Lactobacillus kefir*, ATCC designation 35411, and (iii) an R-configured trialkylsilylethynyl α-alcohol of formula Ia, below:

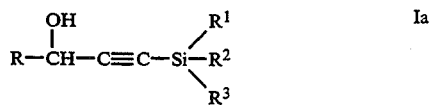

wherein R, its chain length and $R^1$, $R^2$ and $R^3$ are defined as for formula I;

(b) maintaining said reaction mixture under biological reaction conditions and for a time period sufficient to oxidize said R-configured trialkylsilylethynyl α-alcohol and form said trialkylsilylethynyl α-ketone of the corresponding formula.

By appropriately varying the reaction conditions in terms of substrate and cofactor concentrations, the *Lactobacillus kefir* alcohol dehydrogenase enzyme catalyzes the conversion of an alcohol to a ketone. By starting with a trialkylsilylethynyl α-alcohol, the *Lactobacillus kefir* alcohol dehydrogenase produces the corresponding trialkylsilylethynyl α-ketone. Therefore, the present invention provides a novel synthetic route to these important trialkylsilylethynyl compounds.

3. Process of transferring a hydride ion to the pro-R face of NADP

In a manner analogous to that of other alcohol dehydrogenases, *Lactobacillus kefir* alcohol dehydrogenase can catalyze the oxidation of alcohols as well as the reduction of carbonyl substrates. Because *Lactobacillus kefir* alcohol dehydrogenase has specificity for the pro-R face of NADP, the oxidation of an R-configured alcohol involves the transfer of a hydride ion from the alcohol to the pro-R face of NADP.

In accordance with such a method, a reaction mixture is formed by admixing in a liquid medium (i) NADP, (ii) a catalytic amount of *Lactobacillus kefir* alcohol dehydrogenase and (iii) an R-configured alcohol of formula II, below:

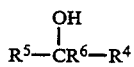

wherein $R^5$ is selected from the group consisting of phenyl, furanyl, thiophenyl, pyridyl, indoyl, biphenylyl, $C_1$-$C_3$ alkylenephenyl, $C_2$-$C_3$ alkenylenephenyl, $C_2$-$C_3$ oxaalkylenephenyl, $C_1$-$C_6$ alkenyl, $C_1$-$C_6$ alkyl, $C_1$-$C_6$ haloalkyl, $C_1$-$C_6$ oxoalkyl, $C_1$-$C_6$ halooxoalkyl, and $C_1$-$C_3$ alkylenecarboxylate;

$R^4$ is hydrogen, $C_1$-$C_6$ alkyl, $C_1$-$C_6$ haloalkyl, $C_1$-$C_4$ trialkylsilylethynyl, $C_1$-$C_6$ azaalkyl, $C_1$-$C_6$ oxaalkyl, $C_1$-$C_6$ alkoxy carbonyl, $C_1$-$C_6$ acyl and $C_1$-$C_6$ oxoalkyl;

or $R^4$ and $R^5$ together form a 5-, 6- or 7-membered saturated or monoethylenically unsaturated ring;

$R^6$ is hydrogen, deuterium or tritium; and the total chain length of a substrate of formula II is three to about 10 carbon atoms.

The reaction mixture is then maintained under biological reaction conditions and for a time period sufficient to oxidize the R-configured alcohol.

In a preferred embodiment, the hydride ion is deuteride ($D^-$) or tritide ($T^-$). Where the hydride ion is ($D^-$) or ($T^-$), the R-configured alcohol substrate used in the method contains deuterium or tritium, respectively, as the hydrogen component of the alcohol hydroxyl group that is oxidized. Deuterium or tritium labelled alcohols can be obtained from commercial sources or made using standard methods well known in the art.

Because the *Lactobacillus kefir* alcohol dehydrogenase used in the process of the present invention adds hydride ion to the pro-R face of NADP, where that hydride ion is ($D^-$) or ($T^-$), the formed NADPH has deuterium or tritium, respectively, only at the pro-R face of the nicotinamide ring. In this regard, a process of the present invention can be used to specifically label the pro-R face of NADPH with deuterium or tritium. That labelled NADPH can then be used to study the mechanism of alcohol dehydrogenase activity using any enzyme and carbonyl substrate.

The stereochemical mechanism of *Lactobacillus kefir* alcohol dehydrogenase with respect to NADP was determined by the enzyme catalyzed transfer of a deuteride ion from 2-propanol-$d_8$ to NADP followed by NMR analysis (See Example 1, hereinafter). Because the diastereotopic hydrogens at $C_4$ of NADPH differ by 0.1 ppm (2.77 ppm for the pro-R facial hydrogen and 2.67 ppm for the pro-s facial hydrogen) the transfer of a deuteride ion to NADP will show a single peak representative of the stereochemistry of hydride transfer. Arnold et al., *Biochemistry*, 15:4844 (1976).

*Lactobacillus kefir* alcohol dehydrogenase transfers the deuteride (and analogously the hydride) to and from the re face of the cofactor as determined by the finding of a single NMR peak at 2.67 ppm.

4. Process of transferring a hydride ion to the si face of a ketone

As already discussed, *Lactobacillus kefir* alcohol dehydrogenase can catalyze the oxidation of alcohols as well as the reduction of carbonyl substrates. Because *Lactobacillus kefir* alcohol dehydrogenase has specificity for the pro-R face of NADPH, the reduction of a ketone involves the transfer of a hydride ion to from the pro-R face of NADPH to the si face of a carbonyl.

In accordance with such a method, a reaction mixture is formed by admixing in a liquid medium (i) NADP, (ii) a catalytic amount of *Lactobacillus kefir* alcohol dehydrogenase and (iii) a ketone of formula IIa, below:

wherein $R^4$, $R^5$ and the total length of the substrate compound of formula IIa are as defined before.

The reaction mixture is then maintained under biological reaction conditions and for a time period sufficient to oxidize the R-configured alcohol.

In a preferred embodiment, the hydride ion is deuteride ($D^-$) or tritide ($T^-$). Where the hydride ion is ($D^-$) or ($T^-$), the NADPH used in the method contains deuterium or tritium, respectively, as the hydrogen component of the NADPH that is oxidized. Deuterium or tritium labelled NADPH can be obtained from commercial sources or made using *Lactobacillus kefir* and deuterium or tritium labeled alcohols according to a process of the present invention. Such labelled NADPH can also be prepared using standard methods well known in the art.

Because the *Lactobacillus kefir* alcohol dehydrogenase used in the process of the present invention adds hydride ion to the si face of a carbonyl, where that hydride ion is (D⁻) or (T⁻), the formed alcohol has deuterium or tritium, respectively, only at the R position of the alcohol. In this regard, the process of the present invention can be used to specifically label the R position of an alcohol with deuterium or tritium. That labelled R-alcohol can then be used to study the mechanism of alcohol dehydrogenase activity using any enzyme and NADP or NAD. Indeed, such a labelled alcohol can be used as a metabolic probe to study the uptake and utilization of alcohols in the growth of, for example, microorganisms. The specificity of any given enzyme system can be readily established using an alcohol with a label at only one position.

The stereochemical mechanism of *Lactobacillus kefir* alcohol dehydrogenase with respect to NADP was determined as discussed elsewhere herein (see Example 1).

Inasmuch as the substrate compounds depicted in formulas I, Ia, II and IIa can contain some of the same substituent groups, the various radicals that can constitute one or more of those substituents will be discussed hereinbelow.

Thus, for the aromatic substituents, phenyl is a substituent benzene ring, furanyl is a 2- or 3-substituted furan ring, thiophenyl is a 2- or 3-substituted thiophene ring, pyridyl is a 2-, 3- or 4-substituted pyridine ring, indoyl is an indole ring that can be substituted at one of six carbon atoms, and biphenylyl is a 2-, 3- or 4-substituted biphenyl ring.

Exemplary $C_1$-$C_6$ alkyl groups include straight and branched chain as well as cyclic radicals such as methyl, ethyl, isopropyl, butyl, sec-butyl, cyclopropyl, cyclohexyl, and 2-hexyl. Exemplary $C_1$-$C_6$ alkenyl groups include straight and branched chain radicals such as vinyl, 1- or 2-propenyl, vinyl, 1-methylvinyl, 1-butenyl, 2-butenyl, and 2-methylpentenyl.

A haloalkyl group is an above alkyl group containing one or more halogens. Exemplary $C_1$-$C_6$ haloalkyl groups are chloroethyl, chloropropyl, trifluoromethyl, trifluoropropyl, 2-chlorohexyl and bromoethyl.

A $C_1$-$C_6$ acyl group is a $C_1$-$C_5$ alkyl group terminated by a carbonyl group that is bonded to the depicted carbonyl or hydroxyl-bearing carbon atom, and as such, the $C_1$-$C_5$ alkyl portion thereof can be a straight or branched chain alkyl group as discussed before.

The presence of an $C_1$-$C_6$ alkoxy carbonyl group provides an α-hydroxy- or α-ketocarboxylic acid ester substrate in which the alcohol portion of the ester is formed from a $C_1$-$C_6$ alkyl alcohol. The alkyl portion of that alcohol is a before-described straight or branched chain $C_1$-$C_6$ alkyl group.

A $C_1$-$C_6$ aza- or oxaalkyl group is a before-described $C_1$-$C_6$ alkyl group, one or two of whose carbon atoms have been substituted for in the alkyl chain by a nitrogen or oxygen atom, respectively. Exemplary groups include 3-aza-3-methylbutyl, 1-(α-oxapropyl)-2-oxabutyl and 1-(α-oxaethyl)-2-oxapropyl radicals.

A $C_1$-$C_3$ alkylenephenyl radical includes a phenyl group linked to one through three carbons, one of which carbons is linked to the depicted carbonyl or hydroxyl-bearing carbon group of a formula. Exemplary $C_1$-$C_3$ alkylenephenyl groups include benzyl, phenethyl and 2-phenylpropyl radicals. A $C_2$-$C_3$ alkenylenephenyl radical is similar to a $C_1$-$C_3$ alkylenephenyl radical except that ethylenic unsaturation is present in the $C_2$-$C_3$ alkenylene group. Exemplary of such groups are vinylenephenyl, 1- and 2-allylenylphenyl and the like. A $C_2$-$C_3$ oxaalkylenephenyl radical has a carbon atom of the alkylene chain replaced by an oxygen atom. Exemplary of such groups are 2-oxaethylenephenyl (2-oxaphenethyl) and 3-oxapropylenephenyl.

A $C_1$-$C_6$ oxoalkyl group is a before discussed alkyl group in which —$CH_2$— has been replaced by a carbonyl group. The presence of a $C_1$-$C_6$ oxoalkyl group provides an additional carbonyl; i.e., ketone or aldehyde, functionality to a compound of formula II or IIa. Exemplary $C_1$-$C_6$ oxoalkyl groups include 2-oxopropyl, 3-oxobutyl and 3-oxohexyl. Similarly, a $C_1$-$C_6$ halooxoalkyl group is a $C_1$-$C_6$ oxoalkyl group containing a further halogen substituent. An exemplary $C_1$-$C_6$ halooxoalkyl group is 1-chloro-2-oxopropyl.

A $C_1$-$C_3$ alkyl $C_1$-$C_3$ alkylenecarboxylate is a $C_1$-$C_3$ alkyl ester of a keto or hydroxyl carboxylic acid of one of the formulas in which the carboxyl group is separated from the illustrated carbonyl or hydroxyl group of a formula by 1-3 carbons of the $C_1$-$C_3$ alkylene group. Exemplary groups include methyl carboxymethyl and methyl carboxyethyl.

A $C_1$-$C_4$ trialkylsilylethynyl group is constituted by a $C_1$-$C_4$ trialkylsilyl radical bonded to one of the carbon atoms of an acetylenyl group whose other carbon atom is bonded to a depicted hydroxyl-bearing carbon atom or carbonyl. Exemplary trialkylsilyl groups so bonded include trimethylsilyl, triethylsilyl, t-butyldimethylsilyl, triiso-propylsilyl, iso-propyldimethylsilyl, and 2-butyldimethylsilyl. Trimethylsilyl is preferred.

It is also to be understood that the carbonyl or hydroxyl group of formulas IIa and II can be present within a ring containing 5-, 6- or 7-members that is saturated except for the depicted keto group of formula IIa or is additionally monoethylenically unsaturated. Put differently, $R^4$ and $R^5$ of formulas II and IIa together form a 5-, 6- or 7-membered ring that is saturated except for a depicted carboxyl group of formula IIa or contains monoethylenic unsaturation. The ring formed from $R^4$ and $R^5$ can also include further substituents such as one or more alkyl groups, a halo group or a phenyl. In the case of phenyl and alkyl groups, those radicals can also be fused into the 5-7-membered ring so that a compound of formulas II or IIa is present as a bicyclic ring system whose carbonyl group-containing ring has 5-7 atoms and whose fused ring contains an additional 1-4 carbon atoms. Exemplary compounds where $R^4$ and $R^5$ together form such ring structures are shown hereinafter in Table 1.

A hydroxyl or carbonyl substrate of formulas II or IIa has an overall length of three to about ten carbon atoms. That is to say that a carbonyl or hydroxyl or substrate is a compound having a length greater than that of acetone and less than that of about 5-decanone. A more preferred length is about four to about eight carbon atoms.

The radical chain lengths are measured along the longest linear carbon chain in the molecule. Where ring structures are present, that length is determined as a projection of the ring onto a plane. Thus, a cyclohexyl group has a "length" about equal to that of a butyl group. An atom in the chain other than carbon such as oxygen, silicon or nitrogen is considered to have the size of carbon.

Such lengths can be readily determined by using published bond angles, bond lengths and atomic radii, as needed, to draw and measure a staggered chain, or by building models using commercially available kits whose bond angles, lengths and atomic radii are in accord with accepted, published values. Radical lengths can also be determined somewhat less exactly by assuming unsaturated bonds to have the same length as saturated bonds and that bond angles for unsaturated bonds are the same as those for saturated bonds, although the above-mentioned modes of measurement are preferred. The lengths are determined as the longest length for the compound.

As used herein, the phrase "R-configured alcohol" means that the hydroxyl group formed by reduction of the carbonyl group of the substrate has the R configuration.

Alcohol dehydrogenase from *Lactobacillus kefir* (*L. kefir*) ATCC No. 35411 utilized herein is referred to equivalently as the enzyme; i.e., *L.kefir* ATCC No. 35411 alcohol dehydrogenase, or as an isolated preparation of that enzyme to encompass both the isolated, purified enzyme and the relatively crude enzyme preparation as obtained from the supernatant of broken, centrifuged cells. That preparation can be present in solid form such as a lyophilized product, or in liquid form in an aqueous medium.

The amount of an isolated preparation of the enzyme used in a process discussed herein is a catalytic amount. As used herein, the phrase "catalytic amount" means that amount of *Lactobacillus kefir* alcohol dehydrogenase at least sufficient to catalyze, in a nonrate limiting manner, the conversion of that enzyme's substrate (e.g., a carbonyl substrate of one of the formulas) to product (an R-configured alcohol), or vice versa.

The catalytic amount of *L. kefir* alcohol dehydrogenase varies according to the nature and concentration of that enzyme's substrate as well as to reaction conditions such as temperature, time and pH value. Means for determining the catalytic amount for that alcohol dehydrogenase of the present invention under preselected substrate concentrations and reaction conditions are well known to those of skill in the art. It is to be understood, however, that more than a catalytic amount can be used to speed the reaction, as where preparative amounts of a desired R-configured alcohol are desired.

For example, for the work described herein, about 1 g of wet cells/3 mL of buffer was admixed with an approximately equal volume of 0.1 mm glass beads to a total volume of about 50 mL. The cells were then disintegrated using 3×3 minute shakes in a bead beater at zero degrees C., and the cell debris was removed by centrifugation. About 8 mL of the resulting supernatant was then admixed with 2.5 mmoles of ketone substrate, 15 mg of NADPH and 1 mL of 2-propanol. A purified form of the enzyme can be obtained as described in Hummel, *Appl. Microbiol. Biotechnol.*, 34:15–19 (1990) in which one unit of the enzyme is defined as the amount of enzyme that catalyzes reduction of one μmole of NADPH/minute.

Admixing comprises mixing each ingredient with each of the other ingredients in a suitable liquid medium to form a reaction mixture. Preferably, the liquid medium is an aqueous solvent. The reaction mixture is maintained under biological reaction conditions of temperature, pH, solvent osmolality, ionic composition and ambient atmosphere for a period of time sufficient to reduce the carbonyl substrate and form the R-configured alcohol, the ketone, NADPH or NADP, as appropriate.

Temperature can range from about 15° C. to about 40° C. Preferably temperature is from about 20° C. to about 40° C. and, more preferably from about 25° C. to about 37° C.

The pH value can range from about 6.0 to about 11.0. Preferably, the pH value is from about 6.5 to about 8.5 and, more preferably about 7.0 to about 7.5. The pH value is maintained by buffers in the liquid medium. The buffer is devoid of chelators that bind enzyme cofactors necessary for enzyme activity. The selection of a buffer is based on the ability of the buffer to maintain pH value at the desired level. Where the pH value is about 7.1, a preferred buffer is TRIS.

The osmolality and ionic composition of the aqueous solvent are designed and selected to solubilize the ingredients of the reaction mixture and to provide cofactors for the enzymes contained in the reaction mixture. The osmolality of the liquid medium preferably ranges from that of distilled water to that of one molar sodium chloride.

This enzyme has excellent stability under reaction conditions, obviating the need for immobilization. However, an increase in the reaction rate of *Lactobacillus kefir* alcohol dehydrogenase catalyzed alcohol formation occurs by including low concentrations of an alcohol solvent such as 2-propanol in the reaction mixture. A typical increase of 15 percent was seen for acetophenone reduction. Therefore, 2-propanol accomplishes several tasks for synthesis. First, it increases the rate of carbonyl substrate reduction. Second, by acting as a cosolvent, 2-propanol can aid in the solubility of some substrates. Third, by regenerating NADPH as set forth hereinafter, 2-propanol can also force the reaction to completion. Exemplary alcohol solvents include 2-propanol, ethanol and sec-butanol.

A water-immiscible, alcohol-, ketone- or aidehyde-free (non-reactive) organic solvent for the carbonyl substrate such as hexane, ethyl ether or benzene is also preferably present in the reaction mixture. That solvent provides a phase transfer medium for a carbonyl substrate and alcohol product (and vice versa) that has only minimal water-solubility, as compared to using a dispersed, but undissolved carbonyl or alcohol reactant. Other water-miscible non-reactive organic solvents such as dimethylformamide (DMF), dimethylsulfoxide and the like can also be present at about 5–10 volume percent to assist in solubilizing the substrate or product.

In a preferred embodiment, the NADPH used in the process of the present invention can be regenerated in the same reaction mixture used (1) to make the R-configured trialkylsilylethynyl α-containing alcohol or (2) to transfer a hydride ion from the pro-R position of NADPH to the si face of a carbonyl group of a ketone. The NADPH is regenerated from a cofactor alcohol substrate via a PED alcohol dehydrogenase catalyzed transfer of a hydride ion from that cofactor alcohol substrate to NADP to form NADPH. Preferably, that cofactor alcohol substrate is ethanol, 1-propanol or 2-propanol. 2-Propanol is most preferred.

Alternatively, that cofactor alcohol substrate can be an R-configured alcohol according to formula II, above. Such a cofactor alcohol substrate is, however, not preferred. Where the cofactor alcohol substrate is an R-configured alcohol according to formula II, the alcohol used as the cofactor is different from the R-configured alcohol formed in the process of the present invention. The cofactor alcohol substrate is selected so as to not interfere with either the production or the recovery of the R-configured alcohol formed.

Thus, for example, the present invention provides a process of forming an R-configured trialkylsilylethynyl α-containing alcohol with the regeneration of NADPH, which process comprises the steps of (a) forming a reaction mixture by admixing in a liquid medium (i) a catalytic amount of NADP, (ii) a catalytic amount of a PED alcohol dehydrogenase preparation, (iii) a cofactor alcohol substrate and (iv) a substrate of the formula I, above; and (b) maintaining said reaction mixture under biological reaction conditions and for a time period sufficient to reduce said substrate and form said R-configured trialkylsilylethynyl α-containing alcohol.

In accordance with this embodiment, PED alcohol dehydrogenase constitutes a good example of a one enzyme catalyzed reaction, where a single enzyme (i.e., PED alcohol dehydrogenase) is responsible for a desired reaction as well as cofactor regeneration. Similarly, PED alcohol dehydrogenase can also serve to regenerate NADP in a process for transferring a hydride ion from an R-configured alcohol to the pro-R face of NADP, which process is set forth above. In accordance with such a process, NADP is regenerated from a cofactor aldehyde or ketone substrate and PED alcohol dehydrogenase. Preferably, the cofactor aldehyde or ketone substrate is acetone.

The reaction time and conditions for the formation of an R-configured alcohol vary with the nature of the carbonyl substrate.

The *Lactobacillus kefir* alcohol dehydrogenase used in the processes of the present invention can accept a wide variety of carbonyl substrates such as ketones and aldehydes, including silicon-containing α-alkylenyl ketones. Relative rates for the reduction of exemplary substrates are summarized below in Table 1.

TABLE 1

| | Compound | Relative rate[a] |
|---|---|---|
| 1 | (phenyl-C(O)-CF3) | 7.6 |
| 2 | (2-pyridyl methyl ketone) | 9.3 |
| 3 | (2-furyl methyl ketone) | 1.8 |
| 4 | (6-methyl-5-hepten-2-one) | 75 |
| 5 | (5-chloro-2-pentanone) | 67 |
| 6 | (cyclopropyl methyl ketone) | 5.9 |

TABLE 1-continued

| | Compound | Relative rate[a] |
|---|---|---|
| 7 | (norbornenone) | 3.6 |
| 8 | (TMS-ynone) [b] | — |
| 9 | (methyl ester TMS-ynone) | 3.7 |
| 10 | (acetophenone) | 6.5 |
| 11 | (3-acetylindole) | 2.4 |
| 12 | (3-acetylbiphenyl) | 4.2 |
| 13 | (1,4-benzodioxane acetyl) | 0 |
| 14 | (dimethoxy furan ketone) | 0 |
| 15 | (3,4-dihydroxy-α-chloroacetophenone) | 0 |
| 16 | (4-hydroxy-γ-chlorobutyrophenone) | 0 |
| 17 | (4-fluoro-γ-chlorobutyrophenone) | vs |

TABLE 1-continued

| | Compound | Relative rate[a] |
|---|---|---|
| 18 | 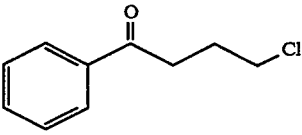 1-phenyl-4-chlorobutan-1-one | 1.1 |
| 19 | 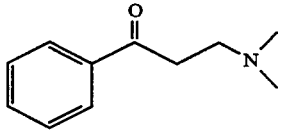 3-(dimethylamino)-1-phenylpropan-1-one | vs |
| 20 | 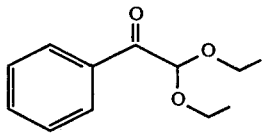 2,2-diethoxy-1-phenylethan-1-one | vs |
| 21 | 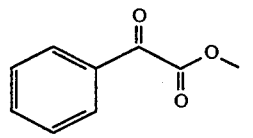 methyl 2-oxo-2-phenylacetate | 0.9 |
| 22 | 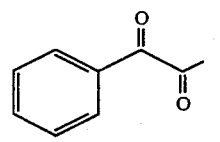 1-phenylpropane-1,2-dione | 19.6 |
| 23 | 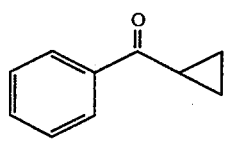 cyclopropyl phenyl ketone | vs |
| 24 | 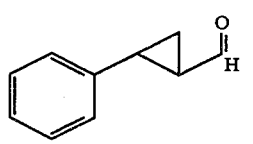 2-phenylcyclopropanecarbaldehyde | 3.2 |
| 25 | 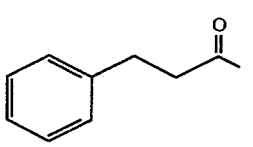 4-phenylbutan-2-one | 23 |
| 26 | 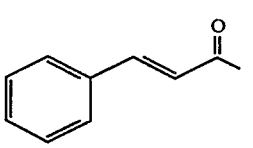 (E)-4-phenylbut-3-en-2-one | 0.2 |
| 27 | 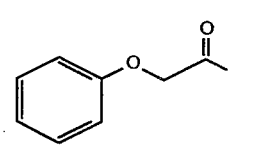 1-phenoxypropan-2-one | 100 |
| 28 | 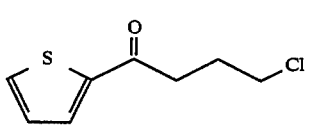 4-chloro-1-(thiophen-2-yl)butan-1-one | 1.4 |
| 29 | 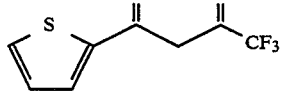 4,4,4-trifluoro-1-(thiophen-2-yl)butane-1,3-dione | 0 |
| 30 | 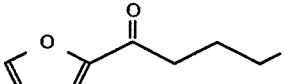 1-(furan-2-yl)pentan-1-one | 0 |
| 31 | 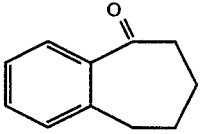 benzosuberone | 0.43 |
| 32 | 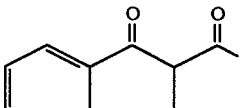 2-acetyl-3,4-dihydronaphthalen-1(2H)-one | 0 |
| 33 | 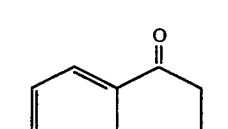 thiochroman-4-one | 0 |
| 34 | 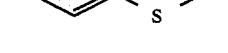 1-benzyl-4-piperidone | 8.2 |
| 35 | 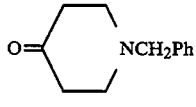 | 0.5 |
| 36 | 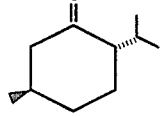 4-tert-butylcyclohexan-1-one | 3.8 |
| 37 | 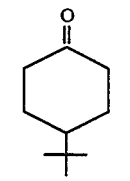 3-chloro-norcamphor | 50 |
| 38 | 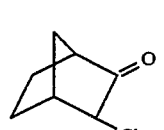 5-norbornene-2-acetyl | 25 |
| 39 | 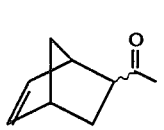 4-cyclopentene-1,3-dione | 0 |
| 40 | 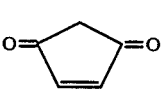 pentane-2,4-dione | 73 |

TABLE 1-continued

| Compound | | Relative rate[a] |
|---|---|---|
| 41 | hexan-2-one structure | 57 |
| 42 | pentan-2-one structure | 53 |
| 43 | ethyl 3-oxopentanoate structure | 16.7 |
| 44 | 1,1-dimethoxypropan-2-one structure | 74 |
| 45 | pent-4-en-2-one structure | 82 |
| 46 | oct-7-en-3-one structure | 2.6 |
| 47 | (E)-4-methoxybut-3-en-2-one structure | 0 |
| 48 | 1-(trimethylsilyl)hex-1-yn-3-one structure | 3.5[b] |
| 49 | 4,4-dimethyl-1-(trimethylsilyl)pent-1-yn-3-one structure | 0.4 |
| 50 | 5-methyl-1-(trimethylsilyl)hex-1-yn-3-one structure | 0.9 |
| 51 | (E)-1-(trimethylsilyl)hex-1-en-4-yn-3-one structure | 1.9 |
| 52 | 1-chloro-4-(trimethylsilyl)but-3-yn-2-one structure | 52 |

[a]Relative rates were determined by arbitrarily setting the rate of reduction for 1-phenoxy-2-propanone to be 100. vs = very slow
[b]TMS = trimethylsilane Previously described alcohol dehydrogenases, including the enzyme from Pseudomonas sp. strain SBD6, typically require that one of the chains of the carbonyl substrate is a methyl group. Although *Lactobacillus kefir* alcohol dehydrogenase can utilize such substrates, it is not necessary that the carbonyl substrate conform to such a structural limitation.

In addition to a methyl side chain, *Lactobacillus kefir* alcohol dehydrogenase of the present invention can utilize a variety of aromatic, aliphatic and cyclic carbonyl substrates. Further, the position of the carbonyl group that is reduced by *Lactobacillus kefir* alcohol dehydrogenase need not be in a fixed position relative to the aromatic side chain. By way of example, 4-phenyl-2-butanone (Compound 25 from Table 1) is a better substrate as measured by relative rate against 1-phenoxy-2-propanone than is acetophenone (Compound 10 from Table 1).

*Lactobacillus kefir* alcohol dehydrogenase can accept a wide range of functional groups attached to the aliphatic ketones. By way of example, *Lactobacillus kefir* alcohol dehydrogenase can catalyze the reduction of silylated terminal alkynyl ketones.

Significantly, *Lactobacillus kefir* alcohol dehydrogenase can accept silicon-containing compounds. This is the first report of the enzymatic reduction of silicon-containing ketones. In fact, enzymatic reductions of organometallic compounds are rare. Sokolov et al., *Gazzetta Chim. Ital.*, 117:525 (1987); Syidatk et al., *Biotechnol. Lett.*, 10:731 (1988); Burgess et al., *J. Am. Chem. Soc.*, 113:6129 (1991). Yields and enantiomeric excesses for the reduction of two of these compounds, Compounds 8 and 9, as well as other representative substrates, is show in Table 2, below.

TABLE 2

| | Starting Material | | Product | | % Yield | % Enantiomeric excess |
|---|---|---|---|---|---|---|
| 1 | phenyl trifluoromethyl ketone | | (S)-1-phenyl-2,2,2-trifluoroethanol | 1a | 71 | >99 |
| 2 | 2-acetylpyridine | | (S)-1-(pyridin-2-yl)ethanol | 2a | 60 | >97 |
| 3 | 2-acetylfuran | | (S)-1-(furan-2-yl)ethanol | 3a | 65 | 95 |

TABLE 2-continued

| Starting Material | | Product | | % Yield | % Enantiomeric excess |
|---|---|---|---|---|---|
| (3-methyl-2-butenyl methyl ketone) | 4 | (R)-alcohol | 4a | 58 | >99 |
| (5-chloro-2-pentanone) | 5 | (R)-alcohol | 5a | 52 | >97 |
| (cyclopropyl methyl ketone) | 6 | (R)-alcohol | 6a | 46 | >97 |
| (norbornenone) | 7 | (R)-alcohol | 7a | 39 | >97 |
| (trimethylsilyl methyl ynone) | 8 | (R)-alcohol | 8a | 25 | 94 |
| (methyl 5-oxo-6-trimethylsilyl-hex-6-ynoate) | 9 | (R)-alcohol | 9a | 15 | 97 |

Silylated (R)-alcohols are formed in good enantiomeric excess. For example, the formation of (R)-1-trimethylsilyl-1-butyn-3-ol (Compound 8a) is produced in 94 percent enantiomeric excess with an unoptimized yield of 25 percent. Higher yields can be obtained with more enzyme or a longer reaction time.

Methyl-4-hydroxy-1-trimethylsilyl-5-hexynoate (Compound 9a) is produced in 97 percent enantiomeric excess with an unoptimized yield of 15 percent. Table 2 shows the yield and enantiomeric excess of other representative carbonyl-containing substrates.

In accordance with this embodiment, *Lactobacillus kefir* alcohol dehydrogenase constitutes a good example of a one enzyme catalyzed reaction, where a single enzyme (i.e., *Lactobacillus kefir* alcohol dehydrogenase) is responsible for a desired reaction as well as cofactor regeneration. Similarly, *Lactobacillus kefir* alcohol dehydrogenase can also serve to regenerate NADPH in other synthetic systems involving NADPH/NADP dependent enzymes.

In all embodiments of the processes of the present invention, the formed ketone, R-configured alcohol, NADP and NADPH each are preferably recovered. Methods of recovering these compounds from liquid media are well known in the art. Exemplary of such methods is paper chromatography.

The following examples illustrate particular embodiments of the invention and are not limiting of the specification and claims in any way.

EXAMPLES

Example 1: Stereochemical Mechanism of *Lactobacillus kefir* Alcohol Dehydrogenase The following were combined and stirred at room temperature: 100 milligrams (mg) NADP, 500 microliters (μL) 2-propanol-d8, and 1 milliliter (mL) (28 units in 50 percent glycerol/phosphate buffer with 0.5 millimolar (mM) MgCl2) of partially purified *Lactobacillus kefir* alcohol dehydrogenase [Hummel, *Appl. Microbiol. Biotechnol.*, 34:15 (1990)]in 5 mL 50 mM ammonium bicarbonate buffer, pH 8, containing 1 mM MgCl2. After three days, the reaction was lyophilized and applied to a DEAE cellulose column (25×1 centimeter [cm]). The unreacted NADP was eluted with 50 mM ammonium bicarbonate and the reduced cofactor was subsequently washed off the column with 250 mM ammonium bicarbonate buffer pH 8. The NADPH fractions were combined, lyophilized, and lyophilized two more times from deuterium oxide. $^1$H NMR (D$_2$O) 2.66 ppm (s, 1H).

The finding of a single NMR peak at 2.67 ppm indicates that *Lactobacillus kefir* alcohol dehydrogenase catalyses the transfer of a hydride ion from an alcohol substrate to the pro-R face of NADP.

Example 2: Synthesis of R-configured alcohols

A. General Materials and Methods

*Lactobacillus kefir* is available from American Type Culture Collection (ATCC 35411), and was grown as recommended by ATCC or as described previously. Hummel, *Appl. Microbiol. Biotechnol.*, 34:15 (1990). Lactobacillus MRS broth is available from Fisher.

All chemicals were purchased from commercial sources (e.g. Aldrich, Fisher, or Sigma). Nuclear magnetic resonance (NMR) spectra were recorded on a 300 MHz spectrometer. (−)-α-Methoxy-α-trifluoromethylphenylacetyl chloride was obtained from Fluka. For the determination of enantiomeric excess, the alcohols were converted to (−)-α-methoxy-α-trifluoromethylphenylacetic acid esters (MTPA esters) and analyzed by NMR spectroscopy, by HPLC analysis on a Daicel chiralcel OB column, or by comparison of the optical rotations versus known compounds. Dale et al., *J. Org.*

B. Enzyme assays

*Lactobacillus kefir* alcohol dehydrogenase enzyme assays were done by combining appropriate aliquots of the following solutions and monitoring at 340 nm ($\epsilon_{NADH}$ 6.22 L mol$^{-1}$ cm$^{-1}$): 50 mM TRIS buffer (DH 7.1), 0.4 mM NADPH and 10 mM of an appropriate carbonyl substrate. Five percent by weight (v/v) of dimethylformamide (DMF) was added to aid substrate solubility.

The enzyme was prepared by suspending the wet cells in 50 mM phosphate buffer, pH 7.5 (1 gram of wet cells per 3 ml buffer), adding an equal volume of 0.1 mm glass beads, and disintegrating the cells 3 times for 3 minutes each time using a bead beater. Cell debris was removed by centrifugation at 15000 rpm for 25 minutes. The supernatant portion was then used as a source of the alcohol dehydrogenase enzyme for subsequent reactions.

A typical reaction mixture was formed by admixing (i) 15 mg NADPH, (ii) 4 ml of 1-propanol and (iii) 2.5 mmoles of a ketone substrate in a liquid medium containing 8 ml of 50 mM phosphate 2 mM magnesium chloride buffer, pH 7.1. When problems of substrate solubility were encountered, the reaction mixture was layered with 10 ml hexane.

The reaction mixture was maintained at room temperature until product formation stopped. When product formation stopped, the aqueous layer was extracted with ethyl ether (3×15 ml).

The combined organic layers were dried over sodium sulfate, evaporated to a residue and the residue purified by chromatography on a silica gel (hexane/ethyl ether) to yield the product.

1. (S)-1-Phenyl-2,2,2-trifluoroethanol (Compound 1a)

When prepared as described above in Example 2.B., the title compound was produced in 71 percent yield and in greater than 99 percent enantiomeric excess (ee) as determined by HPLC analysis on a chiralcel OB column (hexane:2-propanol 98:2). With a flow rate of 1 mL per minute the retention times were 10.65 minutes for (−)(R) and 11.69 minutes for (+)(S). $^1$H NMR (CDCl$_3$) δ 3.15 (bs, 1H); 4.95 (t, 1H); 7.40 (m, 5H). Spectroscopic properties were compared versus literature values for absolute configuration determination ($[\alpha]_D$ +8.6° (C=4.25 benzene), 8 percent enantiomeric excess (ee) of the (S) enantiomer). Peters et al., *J. Org. Chem.*, 33:4245 (1968).

2. (R)-1-(2-Pyridyl)ethanol (Compound 2a)

When prepared as described above in Example 2.B., the title compound was produced in 60 percent yield and greater than 97 percent ee as determined by conversion to a MTPA ester and comparison of the methyl peaks, δ 1.62 and 1.69 for the (S) and (R) isomers, respectively. $[\alpha]_D^{25}$+48° (c=0 75 CDCl$_3$) $^1$H NMR (CDCl$_3$) δ 1.52 (d, 1H); 4.33 (s, 1H); 4.91 (m, 1H); 7.22 (m, 1H); 7.30 (d, 1H); 7.71 (m, 1H); 8.57 (d, 1H). Absolute configuration was determined by comparison of the optical rotation with literature assignments $[\alpha]_D$ +14.7° (C=4.35 ethanol), 22 percent ee for the (R) isomer). Ziffer et al., *J. Org. Chem.*, 48:3017 (1983).

3. (R)-1-(2-Furanyl)ethanol (Compound 3a)

When prepared as described above in Example 2.B., the title compound was produced in 65 percent yield and 95 percent ee as determined by conversion to a MTPA ester and comparison of the methyl peaks, δ 1.62 and 1.69 for the (S) and (R) isomers, respectively. $[\alpha]_D^{22}$+22.0° (c=2.67 CHCl$_3$). $^1$H NMR (CDCl$_3$) δ 1.55 (d, 3H); 1.68 (s, 1H); 4.88 (m, 1H); 6.22 (d, 1H); 6.31 (m, 1H); 7.38 (d, 1H). $^1$H NMR is consistent with the reported values for the (S) enantiomer. Drueckhammer et al., *J. Org. Chem.*, 53:1607 (1988). Absolute configuration was determined by comparison of the optical rotation with literature assignments $[\alpha]_D$+5.0° (C=3.14 CHCl$_3$), 22 percent ee of the (R) isomer). Ziffer et al., *J. Org. Chem.*, 48:3017 (1983); Drueckhammer et al., *J. Org. Chem.*, 53:1607 (1988).

4. (R)-6-Methyl-5-hepten-2-ol (Compound 4a)

When prepared as described above in Example 2.B., the title compound was produced in 58 percent yield and 100 percent ee as determined by comparison of the optical rotation of the (S) enantiomer [literature $[\alpha]_D$+10.76° (CHCl$_3$), 99 percent ee; Keinan et al., *J. Am. Chem. Soc.*, 108:167 (1986)], and conversion to the MTPA ester followed by comparison of the methyl peaks at δ 1.20 and 1.27 for the (S) and (R) isomers, respectively. $[\alpha]_D^{23}$−14.8° C. (c=5, CHCl$_3$). $^1$H NMR (CDCl$_3$) δ 1.20 (d, 3 H); 1.52 (m, 2 H); 1.65 (s, 3H); 1.71 (s, 3H); 2.08 (m, 2H); 3.82 (m, 1H); 5.13 (t, 1H). $^1$H NMR is consistent with the commercially available compound.

5. (R)-5-Chloro-2-pentanol (Compound 5a)

When prepared as described above in Example 2.B., the title compound was produced in 52 percent yield and greater than 97 percent ee as determined by 5 conversion to a MTPA ester followed by comparison of the methyl peaks at δ 1.28 and 1.36 for the (S) and (R) enantiomers, respectively. $^1$H NMR (CDCl$_3$) δ 1.23 (d, 3H); 1.61 (m, 2H); 1.87 (m, 2H); 3.60 (t, 2H); 3.85 (m, 1H). Absolute configuration was determined by comparison of the optical rotation with literature assignments ($[\alpha]_D$+15.58° (CHCl$_3$), 98 percent ee of the (S) isomer). Keinan et al., *J. Am. Chem. Soct*, 108:3474 (1986) .

6. (R)-1-Cyclopropyl-1-ethanol (Compound 6a)

When prepared as described above in Example 2.B., the title compound was produced in 46 percent yield and greater than 97 percent ee as determined by conversion to a MTPA ester followed by comparison of the methyl peaks at δ 1.26 and 1.33 for the (S) and (R) isomers, respectively. $^1$H NMR (CDCl$_3$) δ 0.18 (m, 2H); 0.29 (m, 2H); 0.89 (m, 1H); 1.28 (d, 3H); 3.07 (m, 1H). $^1$H NMR is consistent with the commercially available sample. Absolute configuration was assigned based upon optical rotation of the (R) enantiomer ($[\alpha]_D$−7.55° (CHCl$_3$), 44 percent ee). Keinan et al., *J. Am. Chem. Soc.*, 108:167 (1986).

7. (R)-5-Nornornen-2-ol (Compound 7a)

When prepared as described above in Example 2.B., the title compound was produced in 39 percent yield and greater than 97 percent ee as determined by NMR ratio of endo/exo isomers, δ 4.48 and 3.83 for the endo and exo isomers, respectively. $^1$H NMR (CDCl$_3$) δ 0.78 (m, 1H); 1.28 (m, 2H); 1.49 (m, 1H); 2.12 (m, 1H); 2.83

(s, 1H); 3.01 (s, 1H); 4.48 (m, 1H); 6.11 (m, 1H); 6.46 (m, 1H). ¹H NMR is consistent with the commercially available sample.

8. (R)-1-Trimethylsilyl-1-butyn-3-ol (Compound 8a)

When prepared as described above in Example 2.B., the title compound was produced in 25 percent yield and 94 percent ee as determined by conversion to MTPA ester followed by comparison of the methyl peaks at δ 1.30 and 1.37 for the (S) and (R) isomers, respectively. [α]$_D^{23}$+36° (c=0.47 CDCl₃), ¹H NMR (CDCl₃) δ 0.17 (s, 9H); 1.44 (d, 3H); 1.61 (s, 1H); 4.52 (quartet, 1H). Spectroscopic properties were consistent with those reported previously for the (S) enantiomer ([α]$_D^{25}$−25.9° (C=3.12 CHCl₃), 95 percent ee). Burgess et al., *J. Am. Chem. Soc.*, 113.:6129 (1991).

9. Methyl-4-hydroxy-1-trimethylsilyl-5-hexynoate (Compound 9a)

When prepared as described above in Example 2.B., the title compound was produced in 15 percent yield and 97 percent ee as determined by conversion to a MTPA ester followed by comparison of the methoxy peaks at δ 3.40 and 3.46. ¹H NMR (CDCl₃) δ 0.19 (s, 9H); 1.99 (m, 2H); 2.53 (m, 2H); 3.28 (s, 1H); 3.63 (s, 3H); 4.42 (m, 1H). HRMS: expected, 237.0923; observed, 237.0931. Absolute stereochemistry has not been determined. ¹H NMR is the same as in literature. Lundkvist et al., *J. Med. Chem.*, 32:863 (1989).

Example 3: Synthesis of Trimethylsilcone-Protected Terminal Alkynyl Ketone carbonyl Substrates A. Generally The procedures for the synthesis of these compounds were accomplished as described previously. Walton et al., *J, Organometal. Chem.*, 37:45 (1972).

B. 1-Trimethylsilyl-1-hexyn-3-one ( Compound 48)

Title compound produced in 64 percent yield. ¹H NMR (CDCl₃) δ 0.17 (s, 9H); 0.88 (t, 3H); 1.62 (m, 2H); 2.47 (t, 2H). HRMS: expected, 169.1049; observed, 169.1052. Yogo et al., *Synth. Commun.*, 11:769 (1981).

C. 4,4-Dimethyl-1-trimethylsilyl-1-pentyn-3-one (Compound 49)

Title compound produced in 66 percent yield. ¹H NMR (CDCl₃) δ 0.25 (s, 9H); 1.20 (s, 9H). HRMS: expected, 183.1205; observed, 183.1216. ¹H NMR is the same as reported previously. Birkofer et al., *Chem. Ber.*, 112:2829 (1979).

D. 5-Methyl-1-trimethylsilyl-1-hexyn-3-one (Compound 50)

The title compound was produced in 66 percent yield. ¹H NMR (CDCl₃) δ 0.19 (s, 9H); 0.88 (d, 6H); 2.18 (m, 1H); 2.38 (d, 2H). HRMS: expected, 183.1205; observed, 183.1200. Yogo et al., *Synth. Commun.*, 11:769 (1981); Brinkmeyer et al., *J. Am. Chem..Soc.*, 99:8339 (1977).

E. Methyl-4-oxo-6-trimethylsilyl-5-hexynoate (Compound 9 )

The title compound was produced in 45 percent yield. ¹H NMR (CDCl₃) δ 0.25 ( s, 9H); 2.65 ( t, 2H); 2.89 (t, 2H); 3.69 (s, 3H). HRMS: expected, 213.0947; observed, 213.0947. ¹H NMR is the same as reported previously. Earl et al., *J. Org. Chem.*, 49:4786 (1984).

F. 1-Trimethylsilyl-4-hexen-1-yn-3-one 5 (Compound 51)

The title compound was produced in 84 percent yield. ¹H NMR (CDCl₃) δ 0.23 (s, 9H); 1.98 (d, 3H); 6.14 (d, 1H); 7.19 (m, 1H). HRMS: expected, 167.0892; observed, 167.0881. Merault et al., *J. Organomet. Chem.*, 76:17 (1974).

G. 4-Chloro-1-trimethylsilyl-1-butyn-3-one (Compound 52)

The title compound was produced in 48 percent yield. ¹H NMR (CDCl₃) δ 0.24 (s, 9H); 4.20 (s, 2H). FTIR 2150 cm⁻¹ (m, sharp); 1680 cm⁻¹ (s); 1400 cm⁻¹ (m, sharp); 1260 cm⁻¹ (m, sharp). Birkofer et al., *Chem. Ber.*, 120:1059 (1987).

Although the present invention has now been described in terms of certain preferred embodiments, and exemplified with respect thereto, one skilled in the art will readily appreciate that various modifications,. changes, omissions and substitutions can be made without departing from the spirit thereof.

We claim:

1. A process for transferring a hydride ion from an R-alcohol to the pro-R position of NADP comprising
   (a) forming a reaction mixture in a liquid medium by admixing (i) NADP, (ii) a catalytic amount of the alcohol dehydrogenase enzyme from *Lactobacillus kefir*, ATCC designation 35411, and (iii) an R-alcohol of formula II, below:

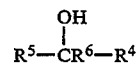

$$R^5-\overset{\overset{\displaystyle OH}{|}}{C}R^6-R^4 \qquad \text{II}$$

wherein

R⁵ is selected from the group consisting of phenyl, furanyl, thiophenyl, pyridyl, indoyl, biphenylyl, C₁-C₃ alkylenephenyl, C₂-C₃ alkenylenephenyl, C₂-C₃ oxaalkylenephenyl, C₁-C₆ alkenyl, C₁-C₆ alkyl, C₁-C₆ haloalkyl, C₁-C₆ oxoalkyl, C₁-C₆ halooxoalkyl, and C₁-C₃ alkylenecarboxylate;

R⁴ is hydrogen, C₁-C₆ alkyl, C₁-C₆ haloalkyl, C₁-C₆ azaalkyl, C₁-C₆ oxaalkyl, C₁-C₆ alkoxy carbonyl, C₁-C₆ acyl and C₁-C₆ oxoalkyl;

or R⁴ and R⁵ together form a 5-, 6- or 7-membered saturated or monoethylenically unsaturated ring;

R⁶ is hydrogen, deuterium or tritium; the total chain length of a substrate of formula II is three to about 10 carbon atoms; and (b) maintaining said reaction mixture under biological conditions and for a time period sufficient to transfer said hydride ion from said R-configured alcohol to NADP and form NADPH and a ketone of the corresponding formula.

2. The process of claim 1 comprising the further step of purifying said NADPH.

3. The process of claim 1 wherein R⁶ is hydrogen.

4. A process for transferring a hydride ion from the pro-R position of NADPH to the si face of a carbonyl group of a ketone comprising
   (a) forming a reaction mixture by admixing in a liquid medium (i) NADPH, (ii) a catalytic amount of the alcohol dehydrogenase enzyme from *Lactobacillus kefir*, ATCC designation 35411, and (iii) a ketone of the formula IIa, below:

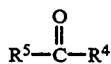

IIa wherein

R⁵ is selected from the group consisting of phenyl, furanyl, thiophenyl, pyridyl, indoyl, biphenylyl, $C_1$–$C_3$ alkylenephenyl, $C_2$–$C_3$ alkenylenephenyl, $C_2$–$C_3$ oxaalkylenephenyl, $C_1$–$C_6$ alkenyl, $C_1$–$C_6$ alkyl, $C_1$–$C_6$ haloalkyl, $C_1$–$C_6$ oxoalkyl, $C_1$–$C_6$ halooxoalkyl, and $C_1$–$C_3$ alkylenecarboxylate;

R⁴ is hydrogen, $C_1$–$C_6$ alkyl, $C_1$–$C_6$ haloalkyl, $C_1$–$C_6$ azaalkyl, $C_1$–$C_6$ oxaalkyl, $C_1$–$C_6$ alkoxy carbonyl, $C_1$–$C_6$ acyl and $C_1$–$C_6$ oxoalkyl;

or R⁴ and R⁵ together form a 5-, 6- or 7-membered saturated or monoethylenically unsaturated ring; the total chain length of a substrate of formula II is three to about 10 carbon atoms; and (b) maintaining said reaction mixture under biological conditions and for a time period sufficient to transfer a hydride ion from said pro-R position of NADPH to said si face of said carbonyl group of said ketone and form NADP and an R-configured alcohol of the corresponding formula.

5. The process of claim 4 comprising the further step of purifying said R-configured alcohol.

6. The process of claim 4 wherein the hydride transferred is H⁻.

* * * * *